United States Patent
Abramov

(10) Patent No.: US 10,118,047 B2
(45) Date of Patent: Nov. 6, 2018

(54) AUTOMATIC DEFIBRILLATION SYSTEM

(71) Applicant: Igor Abramov, Vista, CA (US)

(72) Inventor: Igor Abramov, Vista, CA (US)

( * ) Notice: Subject to any disclaimer, the term of this patent is extended or adjusted under 35 U.S.C. 154(b) by 523 days.

(21) Appl. No.: 14/986,685

(22) Filed: Jan. 3, 2016

(65) Prior Publication Data
US 2017/0189702 A1    Jul. 6, 2017

(51) Int. Cl.
*A61N 1/39* (2006.01)
*A61N 1/05* (2006.01)
*A61N 1/04* (2006.01)

(52) U.S. Cl.
CPC ........... *A61N 1/3918* (2013.01); *A61N 1/046* (2013.01); *A61N 1/0502* (2013.01); *A61N 1/3904* (2017.08); *A61N 1/3925* (2013.01); *A61N 1/3987* (2013.01); *A61N 1/3968* (2013.01)

(58) Field of Classification Search
CPC .. A61N 1/3918; A61N 1/3904; A61N 1/3968; A61N 1/3987; A61N 1/3925; A61N 1/046; A61N 1/0563; A61N 1/0502; A61N 1/0504
See application file for complete search history.

(56) References Cited

U.S. PATENT DOCUMENTS

| | | |
|---|---|---|
| 4,077,413 A | 3/1978 | Partridge |
| 4,785,812 A | 11/1988 | Pihl et al. |
| 5,168,870 A | 12/1992 | Kohl |
| 5,391,187 A | 2/1995 | Freeman |
| 5,405,361 A | 3/1995 | Persson |
| 5,978,714 A * | 11/1999 | Zadini .................. A61N 1/0587 601/41 |
| 6,029,085 A | 2/2000 | Olson et al. |
| 7,242,979 B1 * | 7/2007 | Kelly ................... A61N 1/3937 607/5 |
| 7,272,441 B1 * | 9/2007 | Chapman ............. A61N 1/3931 128/908 |
| 7,277,753 B2 | 10/2007 | Mills et al. |
| 7,920,917 B2 * | 4/2011 | Kelly ....................... A61N 1/39 607/5 |
| 9,126,033 B2 * | 9/2015 | Abramov ............. A61N 1/0587 |
| 9,144,674 B2 * | 9/2015 | Abramov ................. A61N 1/39 |
| 9,531,273 B2 * | 12/2016 | Abramov ............ H02M 3/1588 |
| 2004/0186545 A1 * | 9/2004 | Rosero ................... A61N 1/056 607/119 |
| 2006/0129190 A1 * | 6/2006 | Sullivan ................... A61N 1/39 607/5 |

(Continued)

*Primary Examiner* — Matthew F Desanto

(57) ABSTRACT

Several embodiments of an automatic external defibrillation system (2) comprising external interconnected defibrillator modules (4a) and (4b) are described. The modules (4a) and (4b), upon detection of ventricular fibrillation (VF) by microcomputer (100) via sensing electrodes (26) automatically insert defibrillation electrodes (14) into patient's body (6) and commence delivering defibrillating pulse from the pulse generator (102) to the patient's heart.
An integral defibrillation system (300) having articulating defibrillating elements (4c) and (4d) conforming to patient's body (6) is also described.
Defibrillation electrodes (14) of embodiment (2) are automatically inserted into patient's body in a helical motion, while their counterparts (70) of embodiments (60a) and (60b) are automatically inserted in an essentially downward motion.

15 Claims, 13 Drawing Sheets

(56) References Cited

U.S. PATENT DOCUMENTS

| | | | |
|---|---|---|---|
| 2012/0310315 A1* | 12/2012 | Savage | A61N 1/39 607/116 |
| 2014/0288573 A1* | 9/2014 | Abramov | A61N 1/0587 606/129 |
| 2014/0288574 A1* | 9/2014 | Abramov | A61N 1/0504 606/129 |
| 2015/0306377 A1* | 10/2015 | Brantigan | A61N 1/0504 607/7 |
| 2017/0189702 A1* | 7/2017 | Abramov | A61N 1/3918 |
| 2017/0209691 A1* | 7/2017 | Sorajja | A61N 1/3962 |
| 2018/0085594 A1* | 3/2018 | Tandri | A61N 1/06 |

* cited by examiner

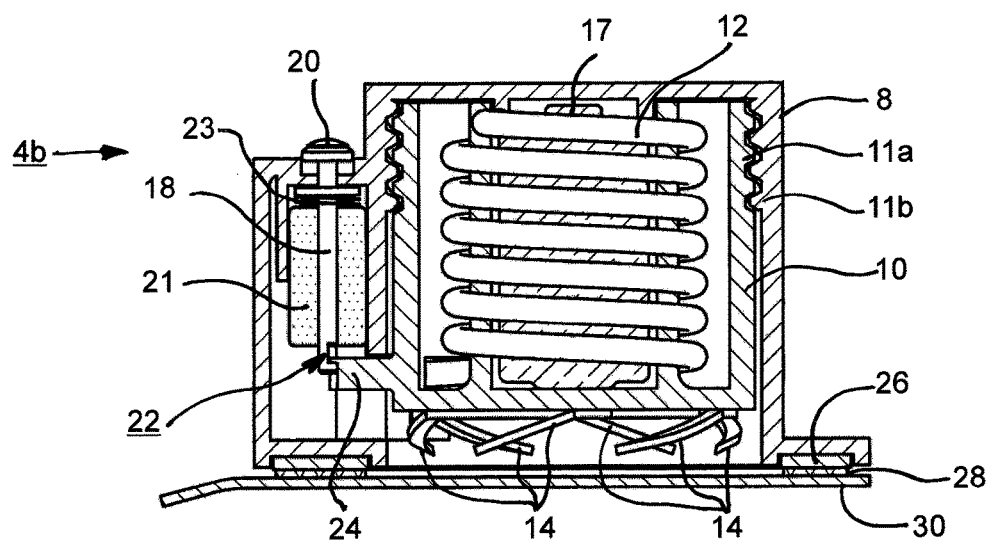
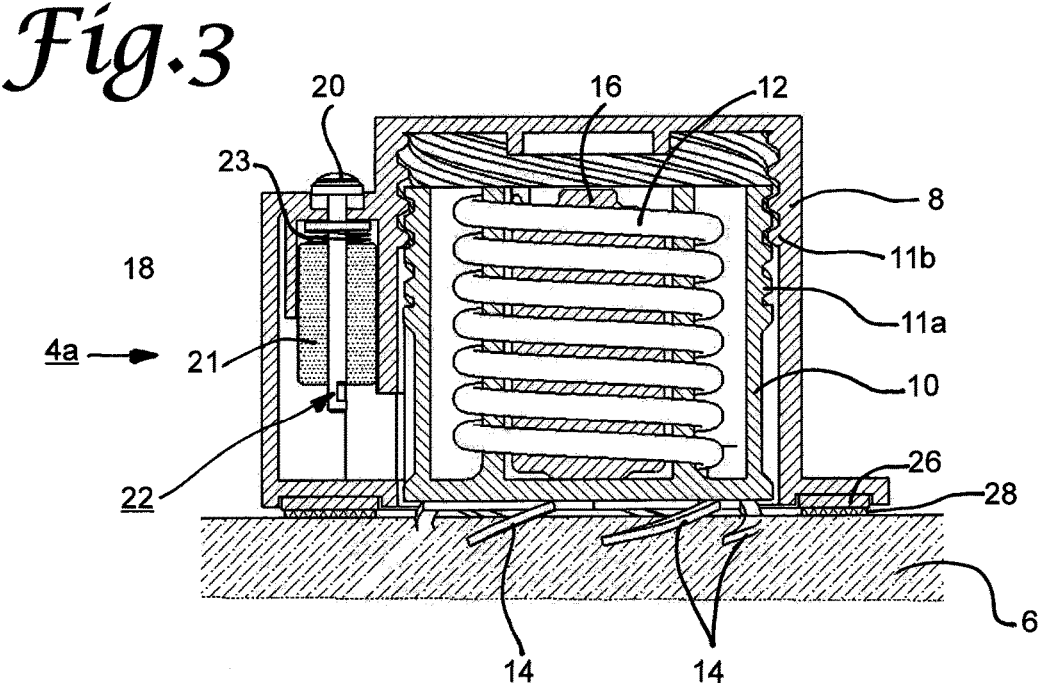

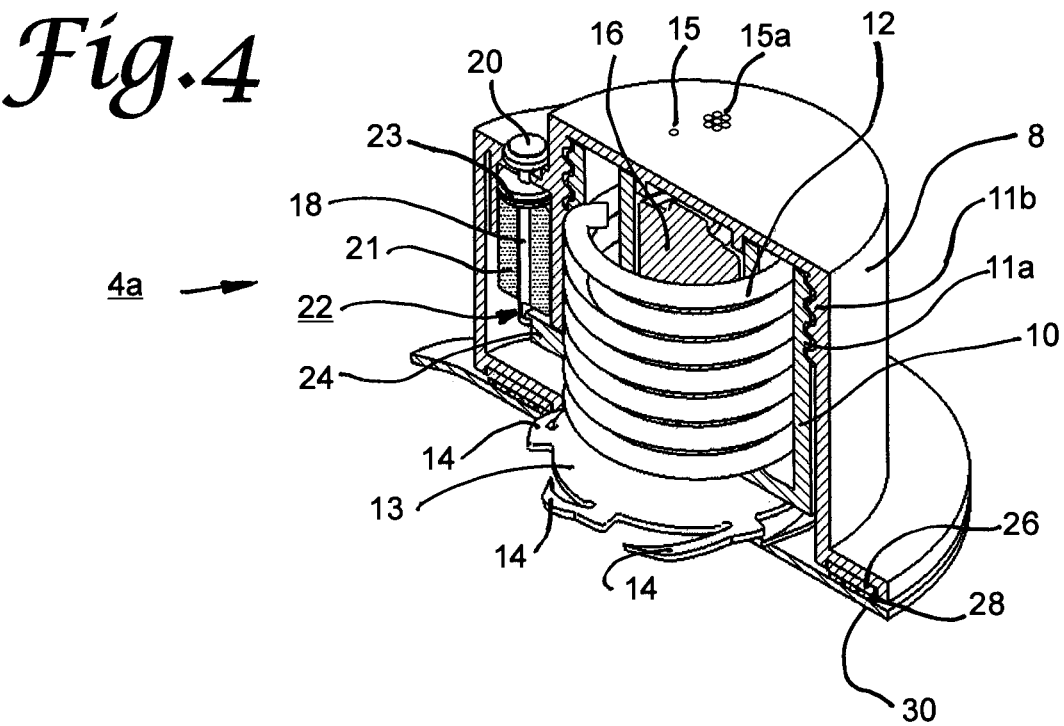
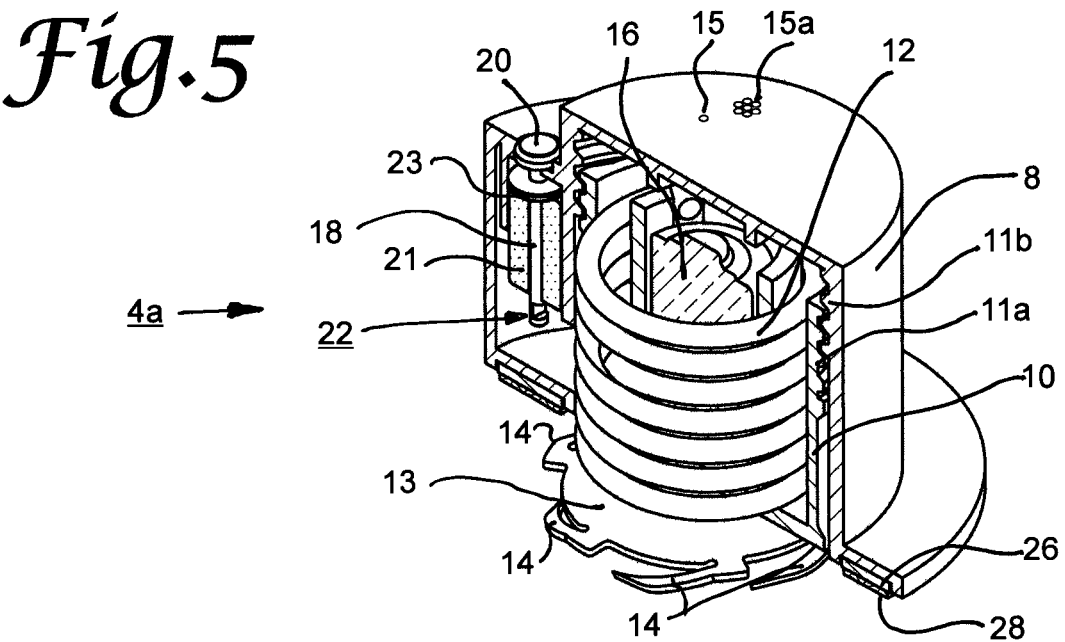

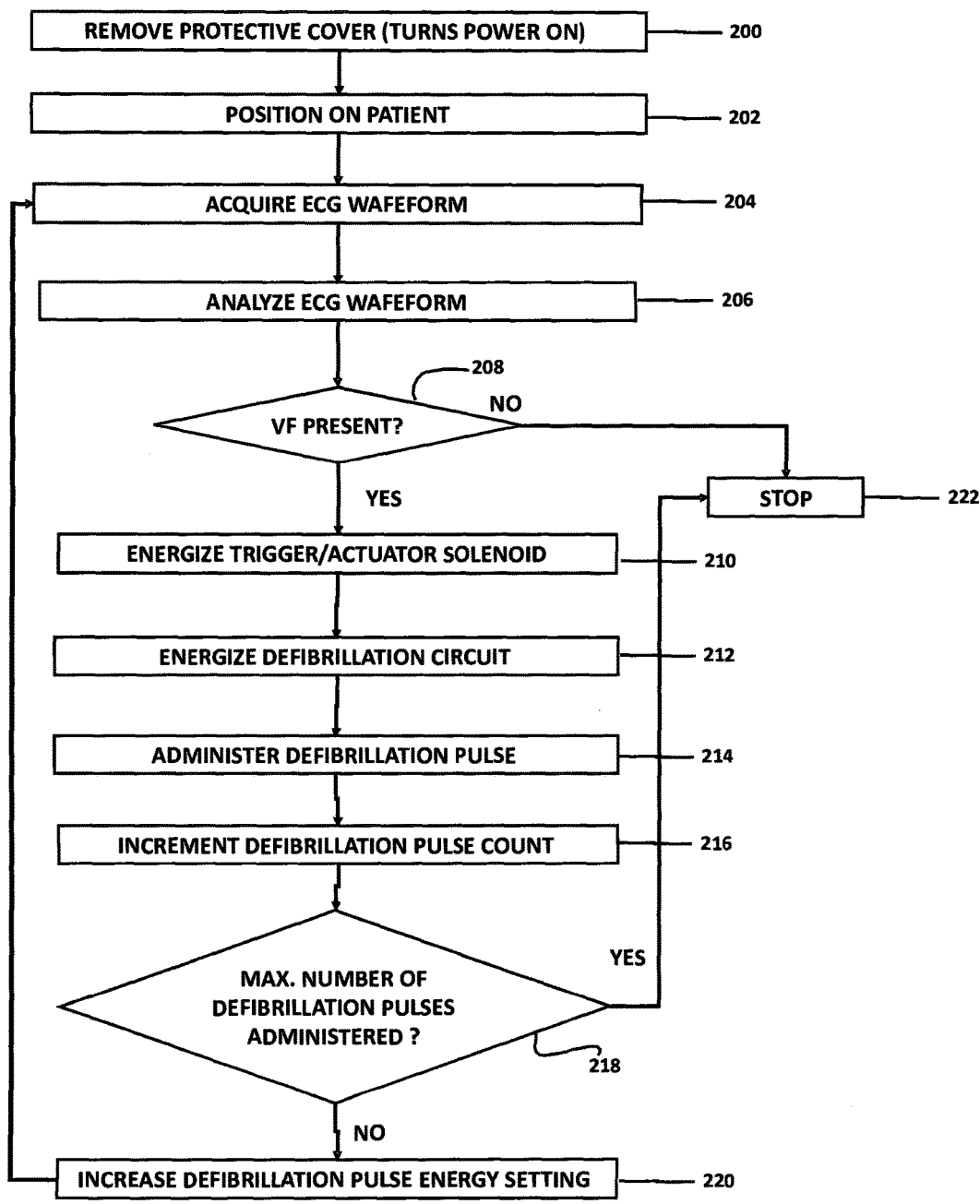

AUTOMATIC DEFIBRILLATION SYSTEM

FIELD OF INVENTION

This invention relates in general to cardiac defibrillators, and in particular to external automatic portable defibrillators.

BACKGROUND OF INVENTION

Modern emergency medical practice strives to provide the most advanced and timely diagnosis and treatment as possible, since time factor is often crucial to the successful clinical outcomes.

One of the sudden critical health crises is cardiac ventricular fibrillation ('VF') which is invariably fatal unless treated promptly. The way to treat VF is to administer an electric pulse to the heart which shocks the heart muscle and induces it to revert to its normal contraction pattern. This procedure is called defibrillation and is effected by a device called 'defibrillator'.

There are two types of defibrillators: the external and internal, the latter implanted into a patient's body.

External defibrillators are relatively large and contain a large battery pack and a high voltage generator. The weight of an external defibrillator is in the order of 2-7 lbs (1-3.5 kg). The generated high voltage pulse is administered to a patient via two large conductive paddles positioned on his chest and side, respectively.

An implantable defibrillator, being very small and light is permanently surgically implanted into a patient's body, and its electrical lead is inserted directly into the heart. The outer case of the device is made of metal and acts as a second electrode to complete the path of electrical current through the heart. The implantable defibrillators are used in patients with chronic cardiac disease and their implantation requires a major surgical procedure in a hospital setting.

In an emergency situation providing an external defibrillator in a timely manner can be problematic, since due to its size and weight it presents a carry challenge to first-response medical personnel who are frequently over-burdened with other equipment and may not have an external defibrillator in their medical kit. Also, some first-responders, such as for example motorcycle patrol policemen may not carry a defibrillator due to the limited carry space on their motorcycles. Waiting for the response team with a defibrillator to arrive may spell death for the VF sufferer, as the chances of survival diminish at the rate of 10% per minute delay. On the other hand, to implant a small defibrillator under non-hospital conditions and within an extremely brief 'window of opportunity' is not feasible.

Still, having a defibrillation capability 'on-hand' in an emergency is very desirable in view of its potential in saving lives.

Through experimentation, I have discovered that when a mammalian epidermis is bypassed, the body electrical impedance is reduced by an order of magnitude. This enables a multifold decrease in the energy required for external defibrillation, bringing it close to the energy provided by implantable defibrillators, and, in turn, results in a much smaller external defibrillator.

OBJECTIVES OF THE INVENTION

Thus, it is the objective of instant invention to provide a small and light automatic external defibrillation system which can be easily carried by a first responder along with other first-aid equipment.

Another objective is to provide an automatic external defibrillation system which would be easy to use.

Yet another objective is to provide an automatic external defibrillation system which could be used by an untrained personnel or public at-large.

SUMMARY OF THE INVENTION

In accordance with the present invention, a miniature automatic external defibrillation system is described. The system consists of interconnected external electronic defibrillator modules integrated with subcutaneous electrode assemblies and surface sensing electrodes. An operator positions the modules near the patient's sternum and laterally preferably below the left armpit.

Via surface electrodes the system then automatically acquires and analyzes a patient heart's electrical activity. In case the system detects ventricular fibrillation (VT), it automatically commences defibrillation procedure.

In preparation to defibrillation the electrodes are automatically inserted subcutaneously which ensures a drastic reduction in the electrical impedance of patient's body and facilitates defibrillation at reduced energy.

After electrode insertion the system commences applying the defibrillation pulse. If no resolution is achieved, the system increases the defibrillation pulse energy and repeats the defibrillation, up to several times, at ever-increasing pulse energies.

The design of the defibrillation modules facilitates simplified operation by an untrained personnel.

The modules also contain redundant manually assisted defibrillation electrode insertion features for increased system reliability.

In addition, the instant invention advantageously offers improved electrical shock protection to the operator by:
a) greatly reduced defibrillation pulse energy and the corresponding much lower voltage, and
b) due to subcutaneous electrode placement, existence of several high-impedance skin barriers: from subcutaneous defibrillation electrodes through patient's skin through operator's skin to operator's heart.

PRIOR ART

The prior art is comprised by two distinct groups of defibrillators: the external and the implantable ones. The external defibrillators, as was mentioned, are quite large and heavy to be truly portable. The implantable defibrillators, while very small and lightweight, are unsuitable in the first-response situations.

OBJECTS AND ADVANTAGES

In contrast to the prior art mentioned hereinabove, the present invention provides a miniature external defibrillator system which delivers the desired defibrillation action at a vastly reduced defibrillation energy.

My research showed that a great difference exists between the required defibrillation energy while using an external defibrillator and using an implanted defibrillator. An external defibrillator is required to deliver up to 400 Joules of electrical energy per pulse. The need for high energy output for external defibrillation results in large size and weight of the corresponding defibrillators. In contrast, only 10-50 Joules per pulse are delivered by an implanted defibrillator with a direct intra-cardiac electrode, with satisfactory defibrillation results.

I determined that the difference in the required pulse energies is due to the high impedance of the human skin and tissues immediately underneath it, which has to be overcome by the existing external defibrillators in order to deliver sufficient defibrillation energy to the heart.

Indeed, through direct experimentation, I discovered that when a mammalian epidermis is bypassed, the body electrical impedance is reduced by an order of magnitude. I call this effect 'DIR', for Dramatic Impedance Reduction. The presence of DIR effect enables a multifold decrease in the energy required for defibrillation which, in turn results in a physically much smaller defibrillator.

An implantable defibrillator, Model S-ICID® made by Boston Scientific, Inc. of Natick, Mass., USA utilizes an indirect subcutaneous electrode positioned along the sternum, with the defibrillator itself implanted laterally, below left armpit. The metal case of this defibrillator serves as a second subcutaneous electrode to complete the current path through the patient's heart. The energy generated by this device is relatively low 80 Joules per pulse but it is sufficient for successful defibrillation. This commercial product further supports the low-impedance model of the subcutaneous electrode operation.

Furthermore, in case of external defibrillators, the external electrode pads by necessity are made quite large in order to decrease impedance and current density and avoid burns to the patient's skin. In case of subcutaneous electrodes, this requirement is reduced due to a lower impedance. Even though, in the instant system embodiments, precautions were taken to decrease current density at electrodes to minimize a chance of an electrical burn injury to the patient.

Conventional external defibrillators present an electric shock hazard to the operators due to the high voltages present during operation and relatively exposed defibrillation electrode pads. Indeed, operators are directed to not touch the patient while defibrillation is taken place, lest electrocution of the operator may result.

In contrast, the defibrillation electrodes of the defibrillation system of instant invention are positioned subcutaneously and are effectively electrically insulated from the patient's outer skin surface. In addition, due to the much lower defibrillation energy required for the defibrillation utilizing the system of instant invention, the defibrillation voltage is decreased multifold as well.

Thus, the combined lower voltage and higher impedance result in a much reduced electric shock risk to an operator.

BRIEF DESCRIPTION OF THE DRAWINGS

FIG. 2a is a cross-section of a second defibrillation module prior to deployment.

FIG. 3 is a cross-section of the first defibrillation module in deployed configuration.

FIG. 4 is a partial cross-section of the first defibrillation module prior to deployment.

FIG. 5 is a partial cross-section of the first defibrillation module in deployed configuration.

FIG. 23 is a simplified flow chart of the defibrillation system operation

DESCRIPTION OF THE EMBODIMENTS

In the foregoing description like components are labeled by the like numerals.

Figure 1:
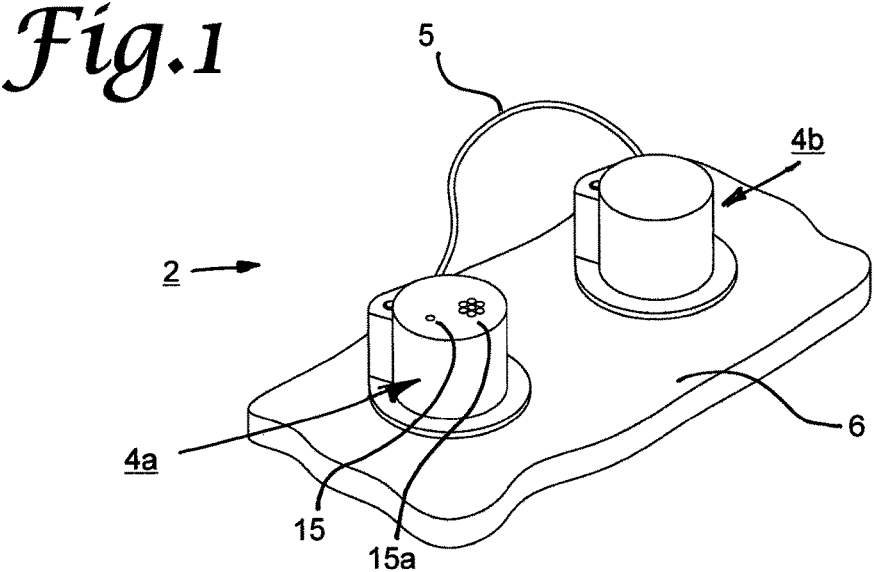
FIG. 1 is a perspective view of the defibrillator system of the instant invention with two defibrillator units deployed.

Referring to FIG. 1 external defibrillation system 2 comprises of two modules, 4a and 4b interconnected by a cable 5. The modules are placed on patient's skin 6.

Figure 2:
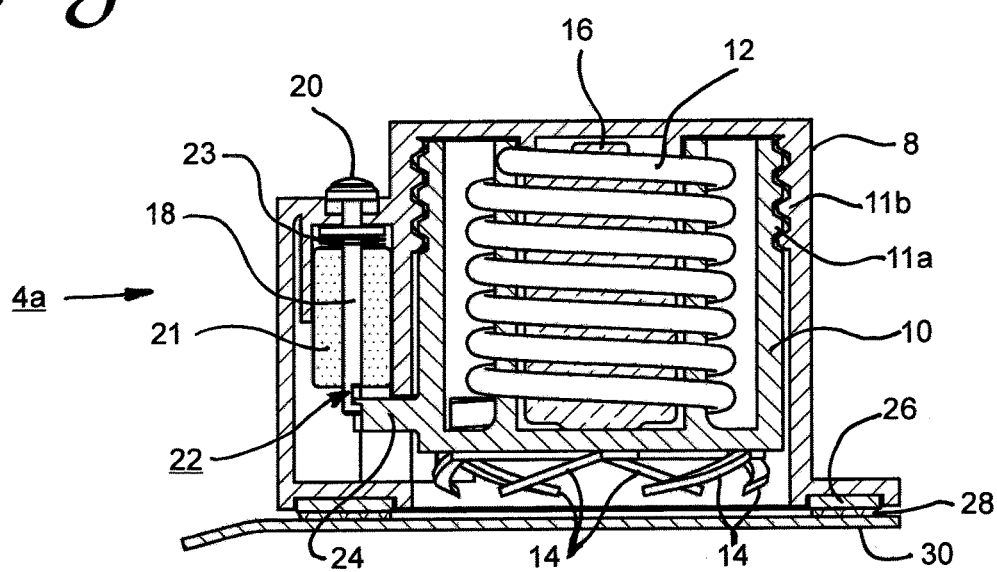
FIG. 2 is a cross-section of the first defibrillation module prior to deployment.
Figure 6:
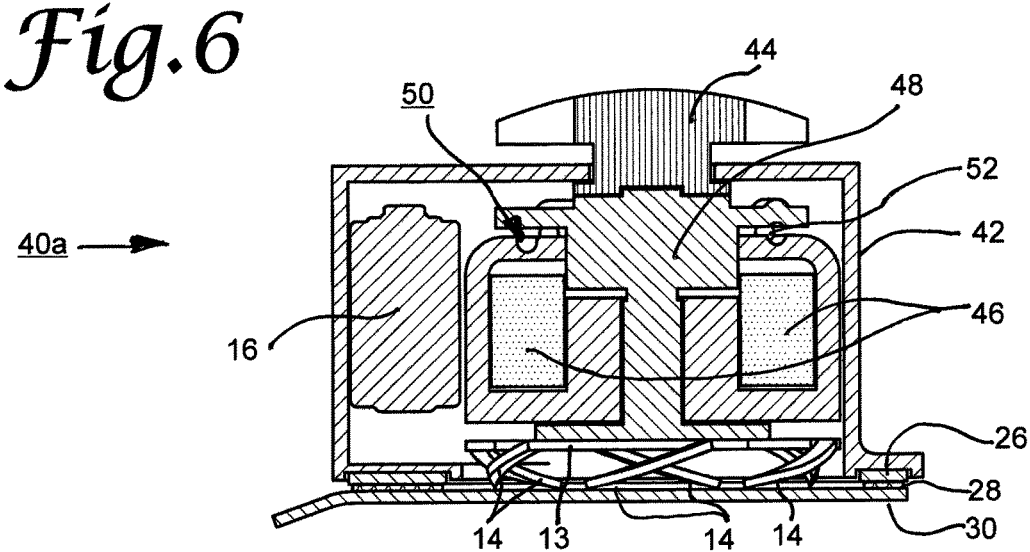
FIG. 6 is a cross-section of an alternative embodiment of the first defibrillation module prior to deployment.

Referring to FIGS. 2, 4 and 5, defibrillation module 4a consists of case 8, which contains battery 16, and an essentially cylindrical cavity inside which an axially rotating assembly 10 is installed and connected to a pre-wound torsion spring 12. Case 8 on its inside surface contains threads 11b which engage corresponding threads 11a of the rotating assembly 10. Case 8 further contains optional visual status indicator 15 and optional audio annunciator 15a.

Case 8 further contains a release solenoid 21 with moving armature 18 which in turn is supported by a return spring 23. Armature 18 contains knob 20 on its top for manual activation of the assembly. Armature 18 further contains release slot 22.

On its bottom case 8 contains an essentially annular sensing electrode 26, covered by an electrically conductive adhesive layer 28.

Rotating assembly further 10 contains a stopping tab 24 and several subcutaneous electrodes 14.

Electrodes 14 and conducting adhesive 28 are sealed prior to activation by a removable protective seal 30.

Figure 16:
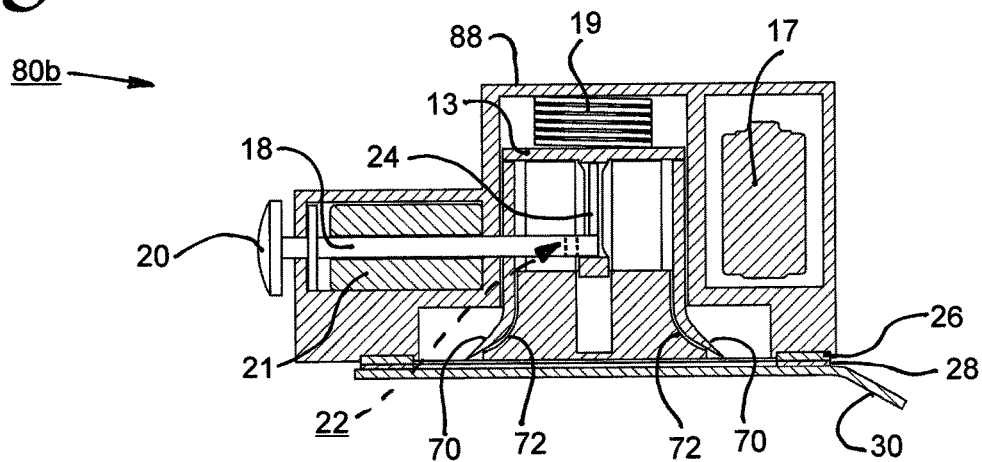
FIG. 16 is a cross-section of an alternative embodiment of the second defibrillation module of an alternate embodiment.

Not shown on the diagram is an insulating tab attached to seal 30 which is connected to switch SW1 on FIG. 16 and prevents connection of the system battery to the rest of the system prior to removal of seal 30, thus averting premature/accidental energizing of the system.

Also not shown is the cable 5 connection inside the unit, nor its connection to the second defibrillator unit.

Referring now to FIG. 2a, a second defibrillator unit 4b is essentially similar to the unit 4a is shown, but with a battery 16 replaced by the electronic subsystem 17.

OPERATION

Referring to FIGS. 2 through 5, at the time of manufacture torsion spring 12 is pre-wound and rotating assembly 10 is rotated into its armed position and secured by stopping tab 24 resting against solenoid armature 18.

Referring now to FIGS. 2 through 5, and 19 through 21, prior to system application, protective seals 30 are removed from both modules 4a and 4b. Although not explicitly shown, this action connects system battery 16 in module 4a to the system's electronics module 17 by switch SW1 and exposes electrically conductive adhesive 28 on the bottom of sensing electrodes 26 of both modules 4a and 4b.

The 4a and 4b modules are placed on patient's skin 6, one preferably on the chest next to the sternum and another preferably laterally under the left armpit.

Conductive adhesive 28 secures modules 4a and 4b onto the patient's skin and his cardiac electrical activity is sensed by sensing electrode 26 of each module.

Microcomputer 100 which is part of electronic module 17 reads patient heart's electrical activity sensed by electrodes 26, analyzes it and determines if ventricular fibrillation (FV) is present. If it is, microcomputer 100 issues a command to turn on release solenoids 21. These solenoids, in addition to solenoids of other embodiments are collectively denoted 104 on FIG. 21.

Solenoid 21 attracts armature 18 which enters solenoid 40 while compressing return spring 23.

Release slot 22 in armature 18 then becomes aligned with stopping tab 24 which passes through it and thus permits rotation (in the drawings, in the clock-wise direction) of assembly 10 by the unwinding of torsion spring 12. Simultaneously, assembly 10 moves downward by cooperative action of coupled threads 11a and 11b in assembly 10 and case 8, respectively.

Electrodes 14 which are part of assembly 10 are inserted by the rotating (clock-wise direction in the drawings) and downward motion of assembly 10 under patient's skin 6 at an oblique angle (FIG. 3)

Figure 21:
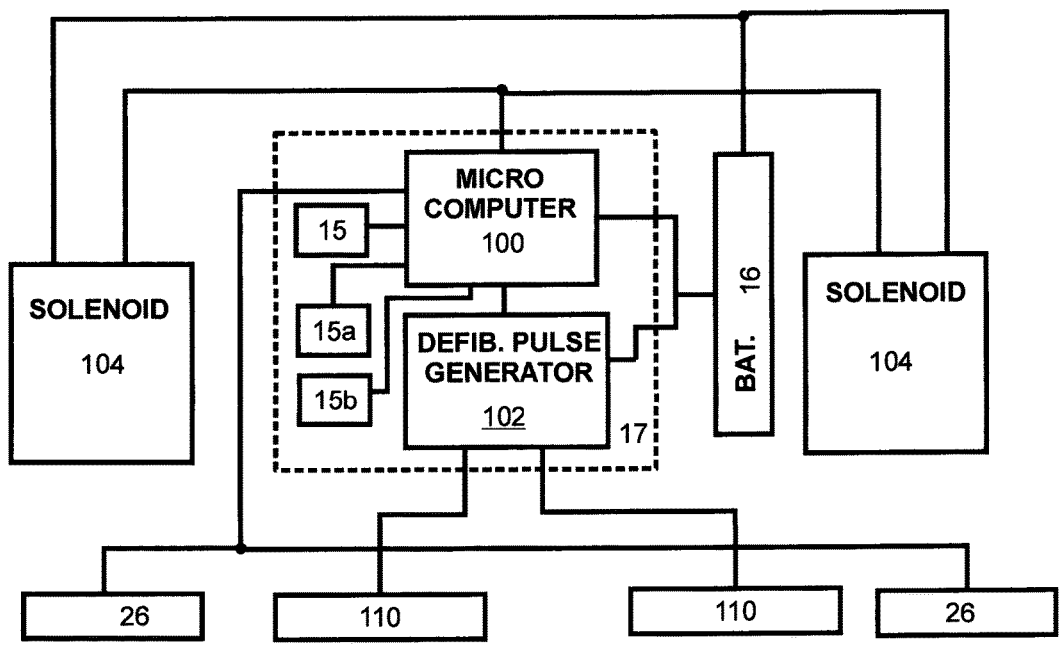
FIG. 21 is a simplified functional diagram of the defibrillation system.
Figure 22:
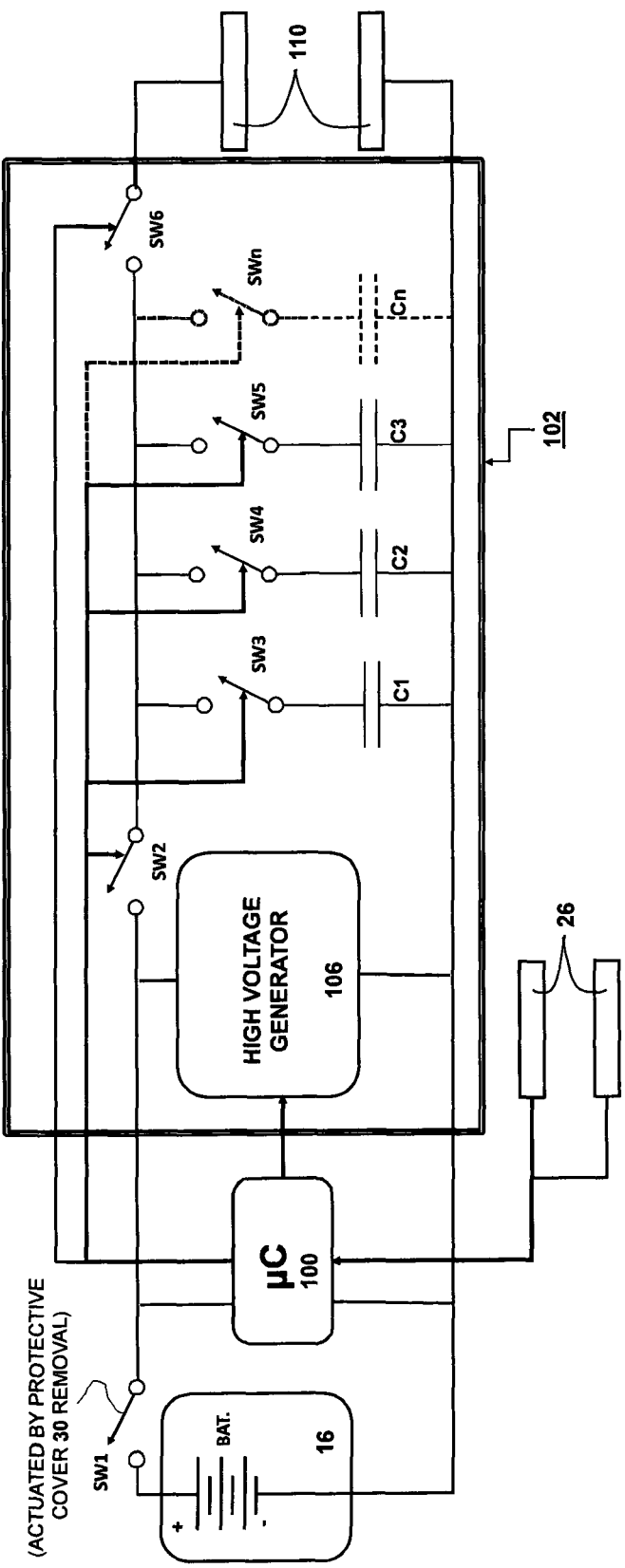
FIG. 22 is a simplified electrical schematic of the defibrillation system.

After electrode placement, referring now to FIGS. 21 through 23, microcomputer 100 issues a command to generate a defibrillation pulse by energizing defibrillation pulse generator 102. The high voltage generator 106 initially charges only capacitor C1 via switches SW2 and SW3 controlled by microcomputer 100. After voltage on capacitor C1 reaches pre-determined defibrillation value, microcomputer 100 opens SW2 to disconnect high voltage generator 106 and closes switch SW6 to transfer the electrical charge stored on capacitor C1 to the defibrillation electrodes collectively labeled 110, thus effecting defibrillation.

Microcomputer 100 then again reads patient heart's electrical activity via sensing electrodes 26 to determine if VF has been resolved. If it is, the units shuts down. If not, microcomputer 100 repeats the defibrillation pulse generation, either at the same or increased energy, depending on the clinical defibrillation protocol selected.

In case of increased pulse energy required, instead of just one C1 capacitor being used, microcomputer 100 connects additional C2 capacitor in parallel to C1 by closing switch SW4 in addition to SW3. The output pulse energy is thus increased through the resulting increase in total capacitance.

The read-charge-defibrillate cycle can be repeated with increasing pulse energy by switching-in additional capacitors C3 through Cn by their respective switches SW5 through SWn under microcomputer 100 control, until either VF condition is resolved or the maximum number or energy of the defibrillation pulse is reached.

Afterwards, the system shuts down and subcutaneous electrodes 14 are removed from the patient by manually rotating 4a and 4b modules counter-clock-wise.

Knob 20 is included on solenoid armature 18 to provide an option to manually trigger rotation of assembly 10 to insert defibrillation electrode 14 if solenoid 21 malfunctions.

If a particular system is so equipped, its status can be monitored by operator via visual indicator 15 and/or audio annunciator 15a which would be both controlled by microcomputer 100. The visual indicator 15 can take a form of a multi-color light-emitting diode (LED) which can flash or change color in accordance to the system's status. Audio annunciator 15a can be a simple piezo-electric buzzer or a miniature speaker announcing the system's status or operating instructions in a natural language.

ADDITIONAL EMBODIMENTS

In the foregoing description like components are labeled with like numerals.

An alternative defibrillator system 2a embodiment utilizing defibrillation modules 40a and 40b is shown on FIGS. 6 through 9.

This embodiment is essentially similar to embodiment 2 in electrical operation, but modules 40a and 40b utilize rotational solenoids 46 to rotate and embed subcutaneous electrodes 14 under patient's skin.

Figure 7:
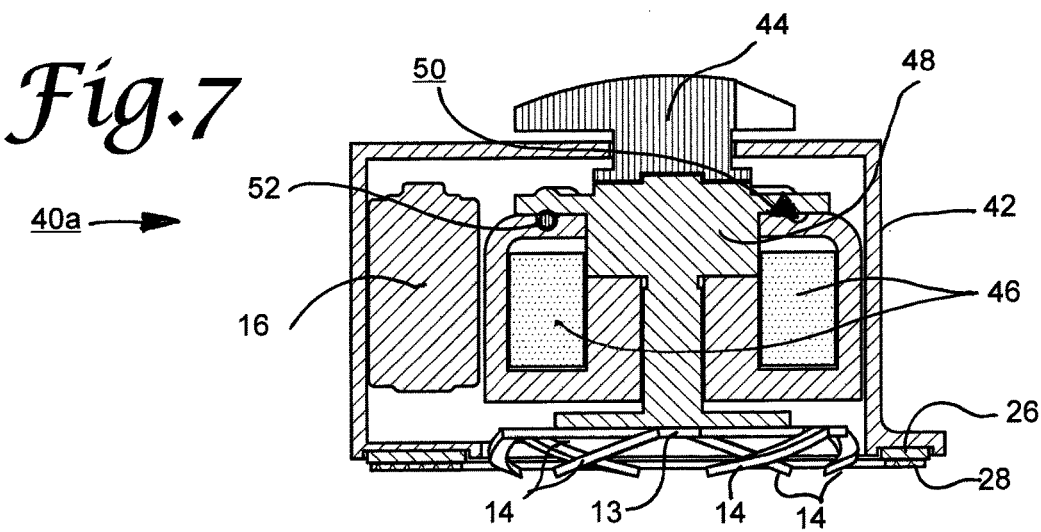
FIG. 7 is a cross-section of an alternative embodiment of the first defibrillation module in deployed configuration.

In module 4a rotational solenoid 46 is located in case 42 which houses battery 16. Solenoid 46 interfaces with armature 48 which rides on several ball bearings 52 located in inclined races 50. When solenoid 46 is energized, armature 48 is pulled towards the solenoid and due to the actions of balls 52 riding in races 50, simultaneously rotates and descends into solenoid 46. Armature 18 on its bottom is connected to defibrillation electrode support assembly 13 which terminates in subcutaneous electrodes 14. Thus, when solenoid 48 is energized, armature 18 rotates and descends, and with it electrodes 14 rotate, descend and obliquely pierce patient's skin (FIG. 7).

Rotational solenoids are well-known and commercially available, for example the Ledex© brand made by Saia-Burgess USA Corporation of Vandalia, Ohio, USA.

Armature 18 on its top is connected to rotational knob 44 which can be manually rotated clock-wise to insert electrodes 14 and is used as a redundant activation feature in case solenoid 46 malfunctions. It can also be used to extract electrodes 14 from patient's skin after conclusion of defibrillation by rotating it counter-clock-wise.

Figure 8:
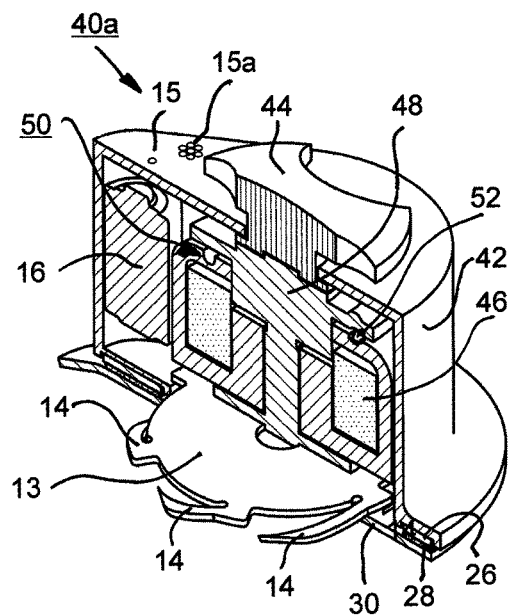
FIG. 8 is a partial cross-section of an alternative embodiment of the first defibrillation module prior to deployment.
Figure 8A:
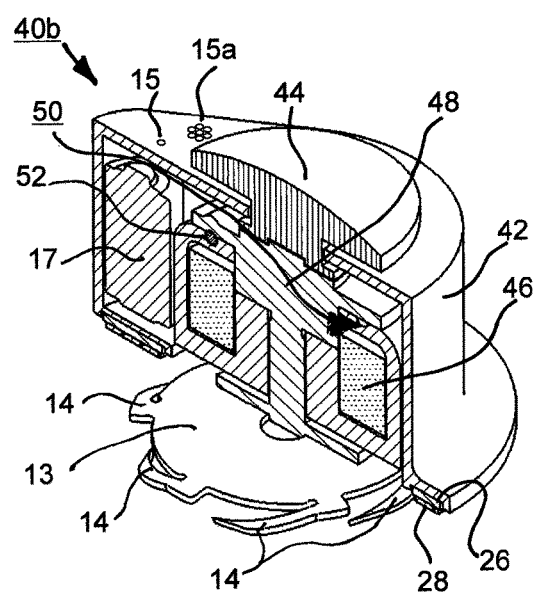
FIG. 8a is a partial cross-section of an alternative embodiment of the second defibrillation module in deployed configuration.
Figure 9:
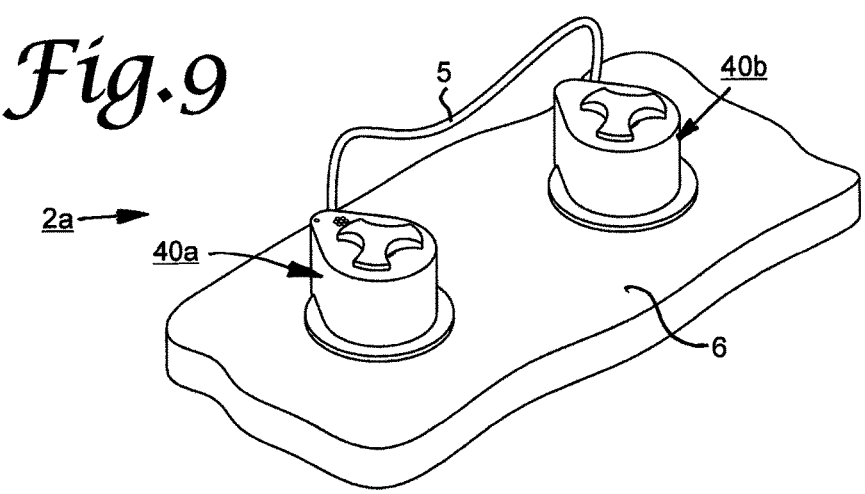
FIG. 9 is a perspective view of an alternative embodiment of the defibrillator system of the instant invention with two defibrillator units deployed.
Figure 10:
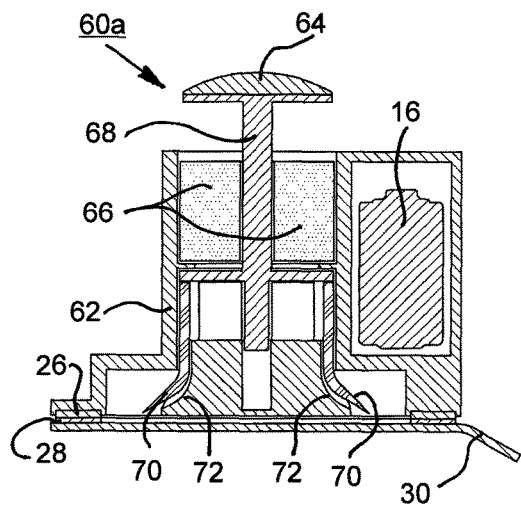
FIG. 10 is a cross-section of an alternative embodiment of the first defibrillation module prior to deployment.
Figure 10A:
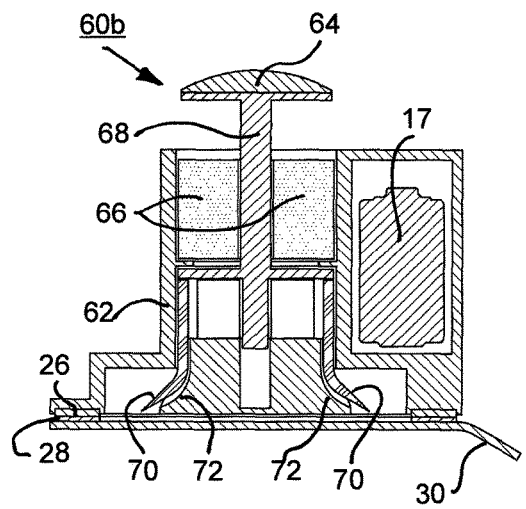
FIG. 10a is a cross-section of an alternative embodiment of a second defibrillation module prior to deployment.

Module 40b in contrast to module 40a contains electronic module 17 instead of battery 16 (FIGS. 8 and 8a).

Alternative embodiments of defibrillation modules 60a and 60b are shown on FIGS. 10 through 14.

Instead of rotationally inserted subcutaneous electrodes 14 of previous embodiments, these modules utilize substantially straight oblique electrodes 70.

Module 60a contains case 62 which houses system battery 16, solenoid 66 and armature 68. Armature 68 is connected on its bottom to several flexible subcutaneous electrodes 70.

Figure 11:
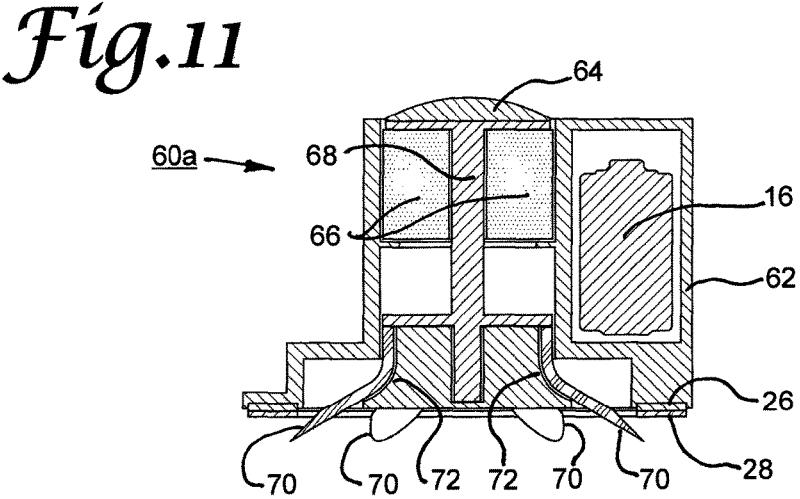
FIG. 11 is a cross-section of an alternative embodiment of the first defibrillation module in deployed configuration.
Figure 12:
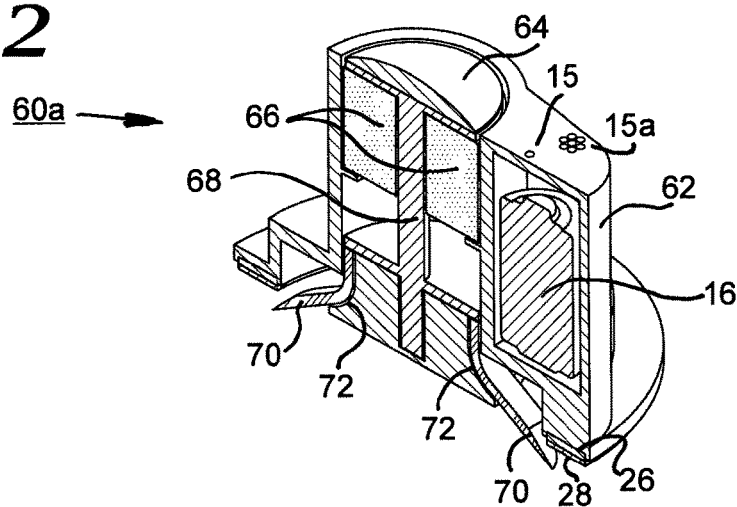
FIG. 12 is a partial cross-section of an alternative embodiment of the first defibrillation module in deployed configuration.
Figure 13:
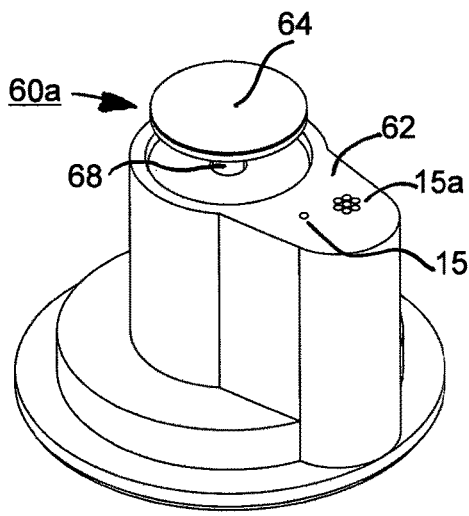
FIG. 13 is a perspective view of an alternative embodiment of the first defibrillation module prior to deployment.
Figure 14:
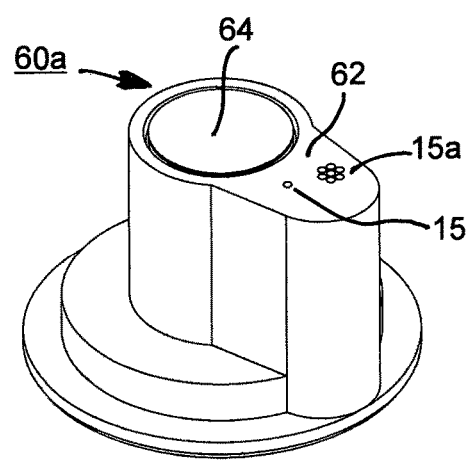
FIG. 14 is a perspective view of an alternative embodiment of the first defibrillation module in deployed configuration.

When solenoid 66 is energized, armature 68 descends and with it electrodes 70. As they advance downward by the action of armature 68, electrodes 70 encounter inclined deflectors 72 and, being flexible, are bent outwards as they follow deflectors' curvature. As a result, electrodes 70 enter patient's skin obliquely and in a controllable manner (FIG. 11).

Armature 68 further contains knob 64 on its top to enable manual electrode insertion in case solenoid 66 malfunctions. It can also be used to remove electrodes 70 from patient's skin.

As in previous embodiments, module 60a contains system battery 16, while module 60b contains electronics module 17.

Figure 15:
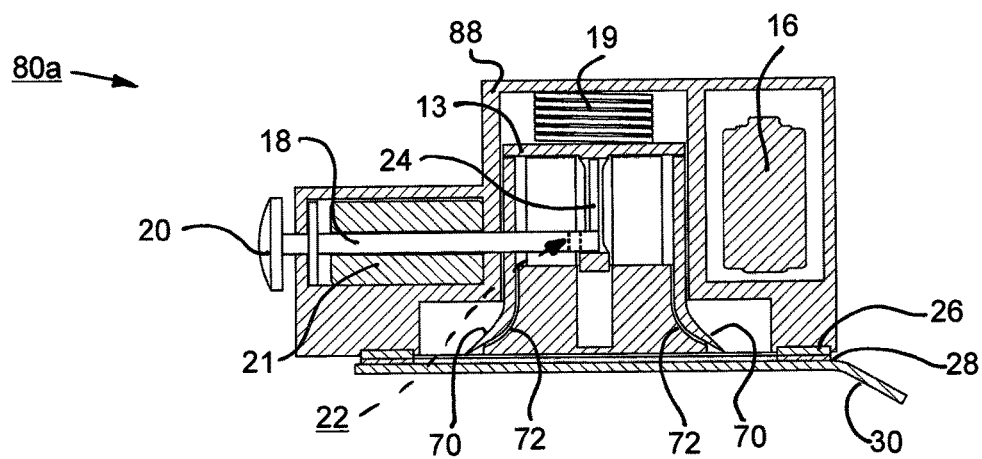
FIG. 15 is a cross-section of an alternative embodiment of the first defibrillation module of an alternate embodiment.
Figure 17:
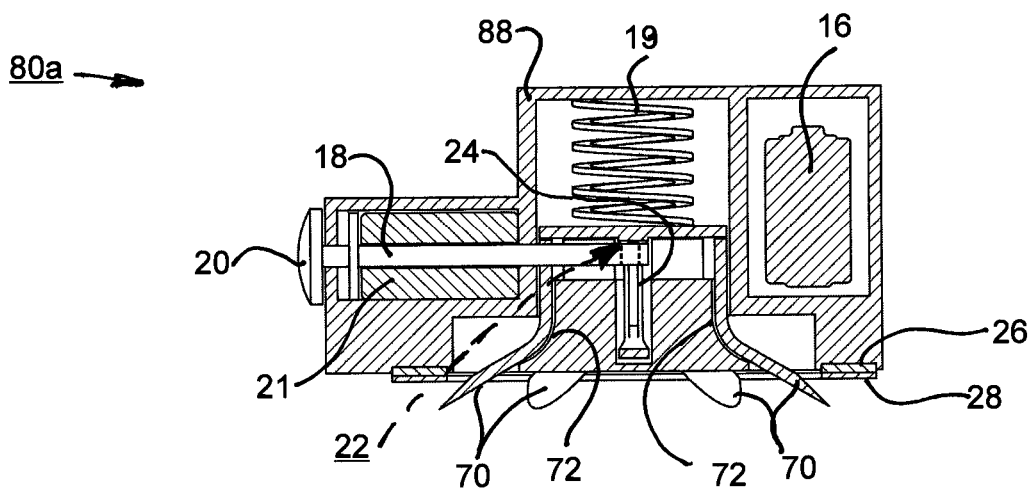
FIG. 17 is a cross-section of an alternative embodiment of the first defibrillation module of an alternate embodiment in deployed configuration.
Figure 18:
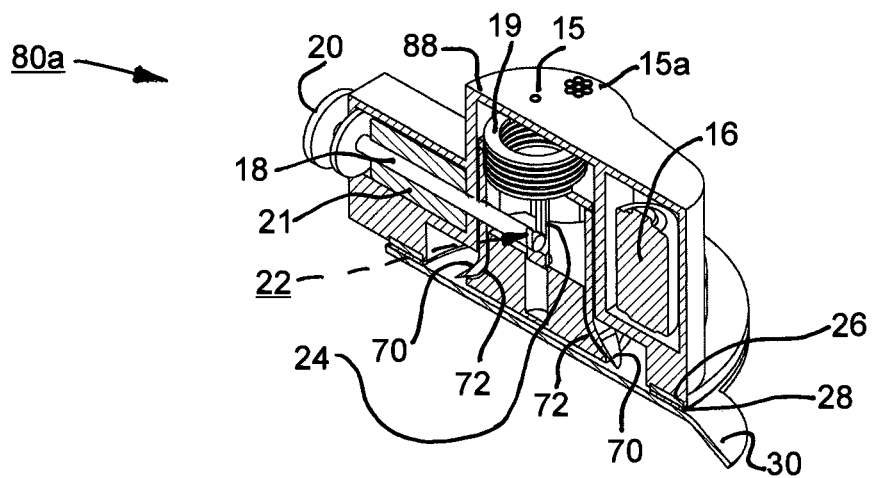
FIG. 18 is a partial cross-section of an alternative embodiment of the first defibrillation module in deployed configuration.

Yet another embodiment, shown on FIGS. 15 through 17 utilizes modules 80a and 80b, and uses springs 19 to embed subcutaneous electrodes 70 in patient's body. Modules' case 88 houses spring 19 which is restrained in the compressed state by armature 18 of solenoid 21 engaging stopping tab 24 of the defibrillation electrode support assembly 13. Armature 18 further contains transverse release slot 22 and knob 20 on its top.

When solenoid 21 is energized by the signal from microcomputer 100, armature 18 is pulled inside of it while its release slot 22 is aligned with stopping tab 24 of the electrode support assembly 13. The released support assembly 13 then moves downward by the action of the expanding spring 19 and electrodes 70 pierce patient's skin, after which defibrillation pulse is administered.

Knob 20 on armature 18 is used for manual activation of the release mechanism in case solenoid 21 malfunctions.

As in previous embodiments, module, 80a contains system battery 16, while module 80b contains electronics module 17.

Figure 19:
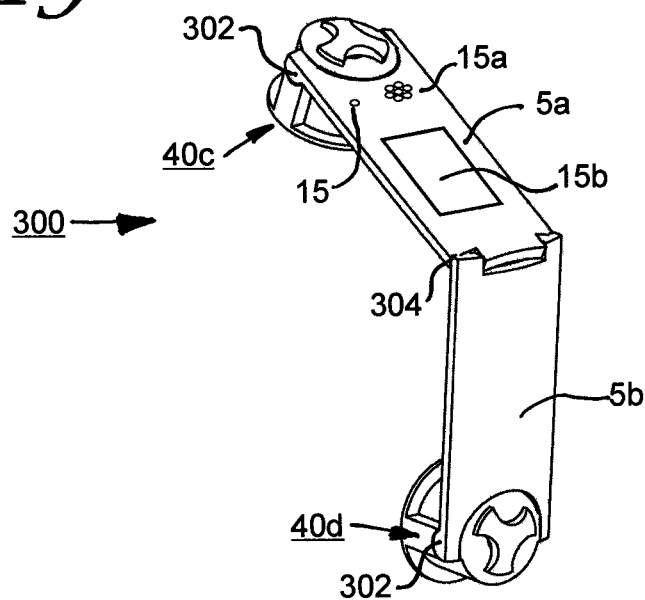
FIG. 19 is a perspective view of an alternative embodiment of the defibrillation system.
Figure 20:
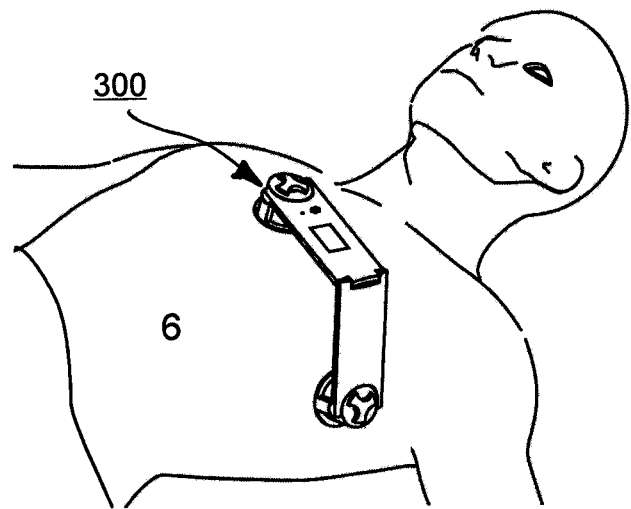
FIG. 20 is a perspective view of an alternative embodiment of the defibrillation system deployed on a patient.

An alternate system embodiment 300 is shown on FIGS. 19 and 21. Two defibrillation modules 40c and 40d are connected to supports 5a and 5b respectively via hinges 302 which enable them to pivot and conform to patient's body 6. Defibrillation modules 40c and 40d are essentially equivalent to the corresponding modules 40a and 40b of embodiment 2a described previously. Supports 5a and 5b are made to pivot around hinge 304 to conform to patient's body 6. In addition to visual indicator 15 and audio annunciator 15a, defibrillator system 300 optionally has a graphic display 15b located in the support 5a.

Electrical conduits functionally similar to cable 5 of previous embodiments are connecting modules 40c and 40d and are contained within supports 5a and 5b.

Although descriptions provided above contain many specific details, they should not be construed as limiting the scope of the present invention.

For example, several features of distinct embodiments can be combined: one defibrillation module may contain both the battery and the electronics module, while another will have just the electrodes.

Also, solenoids of the instant invention, namely the trigger, the rotational and the pushing one can be substituted by miniature electric motors which may offer advantages in weight and size, but potentially at the expense of the speed of activation, energy required for their operation, or overall system reliability.

Subcutaneous electrodes themselves, either for rotational insertion or straight oblique insertion can have varying shapes, thicknesses and sizes, conducive to skin penetration and delivery of the defibrillation pulses.

Also, relatively short straight electrodes for purely vertical insertion are possible if their penetration depth is precisely controlled.

Audio annunciation of the system status and potentially operating instructions can be implemented in various languages and even local dialects by respective firmware executed by the system's microcomputer.

Safety elements, such as restraining rings or tabs can be placed under or next to the manually actuated deployment knobs to prevent accidental deployment of defibrillation electrodes. Such safety elements can be connected to the electrode protective cover, so when the cover is removed, so are the safety elements.

Thus, the scope of this invention should be determined from the appended claims and their legal equivalents.

I claim:

1. An external automatic defibrillator comprising
   a power source,
   a defibrillation pulse generator,
   an electrode insertion mechanism,
   a plurality of defibrillation electrodes attached thereto,
   a microcomputer configured to automatically acquire and analyze a patient heart's electrical activity and automatically commences defibrillation procedure when ventricular fibrillation is detected,
   a plurality of sensing electrodes,
   wherein said sensing electrodes are configured to be placed on patient's body, wherein said microcomputer is configured to acquire patient's heart electrical activity via said sensing electrodes, wherein said microcomputer is configured to analyze said electrical activity for presence of ventricular fibrillation, wherein if said ventricular fibrillation is detected by said microcomputer, said microcomputer automatically initiates defibrillation sequence, said defibrillation sequence comprising the steps of:
   a) automatically energizing said electrode insertion mechanism,
   b) automatically inserting said defibrillation electrodes into said patient's body,
   c) energizing said defibrillation pulse generator,
   d) connecting output of said pulse generator to said defibrillation electrodes and performing defibrillation when ventricular fibrillation is detected.

2. The defibrillator of claim 1 further comprising a defibrillation pulse energy adjusting circuit.

3. The defibrillation pulse energy adjusting circuit of claim 2 comprising plurality of capacitors, said capacitors capable of being interconnected by switches, said switches controlled by said microcomputer to effect various total capacitances.

4. The defibrillator of claim 1 wherein said electrode insertion mechanism comprises a stationary case, a torsion spring, a rotating assembly, said assembly comprising a stop tab, a trigger linear solenoid, said trigger solenoid further comprising moving armature, said armature comprising an essentially elongated rod, said armature further comprising a transverse slot on it distal end, said assembly interfacing with the first end of said torsion spring, wherein the second end of said torsion spring being connected to said stationary case, said torsion spring wound prior to assembly of said mechanism, said torsion spring urging said rotating assembly to rotate, said rotating assembly prior to actuation of said electrode insertion mechanism prevented from rotating by interaction of said stop tab of said rotating assembly and said armature of said trigger solenoid, said armature being attracted into said solenoid upon energizing of said solenoid during actuation of said electrode insertion mechanism, wherein said stop tab in said rotating assembly is aligned with said slot in said armature which action permits rotation of said rotating assembly upon urging of said wound torsion spring while said torsion spring unwinds, wherein said assembly is configured to urge said defibrillation electrodes into said patient's body.

5. The defibrillator of claim 4 wherein said defibrillation electrodes comprise essentially arcuate lamellae, said lamellae is configured to essentially follow a helical path while being inserted into said patient's body.

6. The defibrillator of claim 1 wherein said electrode insertion mechanism comprises a rotational solenoid, said solenoid positioned with its axis of rotation essentially perpendicular to the surface of said patient's skin, said solenoid comprising a rotating armature, said armature is configured to rotate upon energizing of said solenoid and urge said defibrillation electrodes into said patient's body.

7. The defibrillator of claim 6 wherein said defibrillation electrodes comprise essentially arcuate lamellae, said lamellae is configured to essentially follow a helical path while being inserted into said patient's body.

8. The defibrillator of claim 1 wherein said electrode insertion mechanism comprises a case, a linear solenoid, said solenoid comprising moving armature, said armature connected to said subcutaneous defibrillation electrodes, said solenoid configured to be positioned essentially perpendicular to the surface of said patient's skin, said armature configured to insert said defibrillation electrodes into said patient's body upon energizing of said solenoid and moving in a direction essentially perpendicular to—and towards the surface of said patient's body.

9. The defibrillator of claim 8 wherein said subcutaneous defibrillation electrodes comprise essentially elongated flexible lamellae, said case having electrode aligning elements, wherein said defibrillation electrodes are configured to follow said electrode aligning elements and penetrate said patient's body at an essentially oblique angle.

10. The defibrillator of claim 1 further capable of delivering several defibrillation pulses of varying energy.

11. The defibrillator of claim 1 further comprising a visual indicator, said indicator being controlled by said microcomputer, said indicator advising operator of the status of said system and optional instructions for said operator.

12. The defibrillator of claim 1 further comprising audio annunciator, said annunciator being controlled by said microcomputer, said annunciator capable of announcing the status of said system and optional instructions for the operator.

13. The defibrillator of claim 1 further comprising means for manual activation in case said electrode insertion mechanism malfunctions.

14. A defibrillation system comprising at least two defibrillation modules, the at least two defibrillation modules including a first defibrillation module and a second defibrillation module,
   wherein said first module comprises a power source,
   wherein said second module comprises a microcomputer configured to automatically acquire and analyze a patient heart's electrical activity and automatically commences defibrillation procedure when ventricular fibrillation is detected,
   a defibrillation pulse generator,
   wherein said first and said second defibrillation module each further comprises: a plurality of defibrillation electrodes, said defibrillation electrodes insertable into patient's body, said defibrillation electrodes electrically connectable to said defibrillation pulse generator,
   at least one sensing electrode,
   an electrode insertion mechanism, said insertion mechanism capable of automatically inserting said defibrillation electrodes into said patient's body upon command by said microcomputer,
   wherein said microcomputer configured to sense said patient's heart electrical activity with said sensing electrodes,
   wherein said microcomputer configured to analyze said heart electrical activity for presence of ventricular fibrillation,
   wherein said microcomputer is configured to
   commence the following actions: a) automatically energizing said electrode insertion mechanism, b) automatically insert said defibrillation electrodes into said patient's body, c) energizing said defibrillation pulse generator, d) connecting output of said pulse generator to said defibrillation electrodes and performing defibrillation when ventricular fibrillation is detected.

15. The system of claim 14 further comprising means for manual activation in case said electrode insertion mechanism malfunctions.

\* \* \* \* \*